United States Patent [19]

Watanabe et al.

[11] Patent Number: 4,681,633
[45] Date of Patent: Jul. 21, 1987

[54] HIGH STRENGTH CALCIUM PHOSPHATE GLASS-CERAMIC MATERIALS

[75] Inventors: Akira Watanabe, Okayama; Yoshimitsu Takeuchi; Seiji Kihara, both of Bizen; Makoto Mitsudoh, Okayama; Yoh'ichi Wakabayashi, Akasaka, all of Japan

[73] Assignee: Kyushu Refractories Co., Ltd., Okayama, Japan

[21] Appl. No.: 844,249

[22] Filed: Mar. 24, 1986

Related U.S. Application Data

[63] Continuation of Ser. No. 628,748, Jul. 9, 1984, abandoned.

[30] Foreign Application Priority Data

Oct. 29, 1983 [JP] Japan ................... 58-203546

[51] Int. Cl.$^4$ ............................................. C03C 10/02
[52] U.S. Cl. ...................................... 106/35; 501/10; 433/202.1
[58] Field of Search ................ 501/10, 1, 27; 106/35; 433/203

[56] References Cited

U.S. PATENT DOCUMENTS

| | | | |
|---|---|---|---|
| 3,400,097 | 9/1968 | Weinstein et al. | 433/203 |
| 4,167,417 | 9/1979 | Franz et al. | 433/203 |
| 4,189,325 | 2/1980 | Barrett et al. | 433/203 |
| 4,308,064 | 12/1981 | Takami et al. | 501/1 |
| 4,309,485 | 1/1982 | Kondo et al. | 428/457 |
| 4,366,253 | 12/1982 | Yagi | 501/10 |
| 4,417,912 | 11/1983 | Abe | 501/10 |
| 4,431,451 | 2/1984 | Mabie et al. | 106/35 |

FOREIGN PATENT DOCUMENTS 55-11625  3/1980  Japan .

OTHER PUBLICATIONS

Stecher, P. G., "New Dental Materials", pub. 1980 by Noyes Data Corp., Park Ridge, N.J., p. 110.
Phillips, R. W.–"Skinner's Science of Dental Materials", 8th ed, pub. 1983, W. B. Saunders Co., Phila., p. 503.

*Primary Examiner*—Mark L. Bell
*Attorney, Agent, or Firm*—Koda and Androlia

[57] ABSTRACT

Calcium phosphate glass-ceramics of high strength and toughness is disclosed. These materials are excellent for artificial dental or bone materials. The strength and toughness of these materials are improved substantially in comparison with conventionally used calcium phosphate glass-ceramics by adding rare earth oxide in them. For dental materials, good aesthetic appearance to natural teeth is also obtained by adding one type, or two or more types of compounds selected from oxides of iron, manganese, cerium, titanium, nickel, zinc, cobalt, tungsten, chromium, and vanadium as color component. Also, if necessary, $Al_2O_3$ and/or $SiO_2$ is contained as coloring assistant agent in that composite. Moreover it is possible to adjust the color tone of each individual's teeth. The rare earth oxide, coloring component, and coloring assistant agent added are incorporated in crystals of calcium phosphate. Consequently, they cause no elution during use.

1 Claim, No Drawings

HIGH STRENGTH CALCIUM PHOSPHATE GLASS-CERAMIC MATERIALS

This is a continuation of application Ser. No. 628,748, filed July 9, 1984, now abandoned.

BACKGROUND OF THE INVENTION

1. Field of the Invention

This invention relates to materials with calcium phosphate glass-ceramics having high strength and toughness, and more particularly to materials for dental and medical uses.

2. Prior Art

Materials used conventional for restoration of tooth-crowns, tooth-roots, bones, etc. have been metals and plastics. However, these materials have the following defects. That is, they are seriously poor in affinity with the living body, while such affinity is one of the most important characteristics as medical material. Furthermore, depending on conditions of their use, metals or plastics are eluted out, thus causing harmful effects on the living body. Recently, with the purpose of solving these problems, attempts are being made to use ceramic materials, such as alumina, for the foregoing dental and bone materials. However, these ceramic materials are better than the former only in that they are not harmful to the living body, and they are also low in affinity with the living body.

As the materials which are free of the above-mentioned defects of various types of materials, calcium phosphate glass-ceramics are offered. These calcium phosphate materials are ideal as dental and bone materials in light of their characteristics, because, as natural teeth and bones, these materials are composed primarily of phosphorus and calcium, and are high in affinity with gingival tissue. During use, elution of the material components due to saliva, food, etc. is not caused, and even if it is caused, the eluted material components do not affect the human body at all because they are identical to the components of natural teeth and bones. Moreover, their melting points are similar to those of metallic materials. Accordingly, they can be cast by the lost wax process.

The disadvantages of such excellent calcium phosphate glass-ceramics are that they have been regarded to have drawbacks such a low degree of strength and a tendency of easily breaking (brittleness). However, when calcium phosphate glass is crystallized, it becomes stronger than glass and also the brittleness of glass can be reduced. Thus, the foregoing problems can be solved considerably. Nevertheless, in using calcium phosphate crystals as dental and bone material, there are cases where further improved strength is required. In particular, as to toughness, although it is upgraded noticeably in comparison with glass through crystallization, it is still not high enough in degree.

SUMMARY OF THE INVENTION

The present invention was completed after various studies conducted by the inventors with the foregoing facts in mind.

The object of this invention is to provide materials using calcium phosphate glass-ceramics with high strength and toughness for dental and other medical uses.

In keeping with the principles of this invention, the objects are achieved as follows. Into the composites of starting materials, rare earth compounds are added to effect the further improvement in strength as well as toughness of the calcium phosphate glass-ceramics.

With the purpose of improving the strength and toughness of the calcium phosphate glass-ceramics compounds of rare earth elements are added into the glasses prior to crystallization. The added rare earth compounds are dispersed by becoming oxides during the vitrification of calcium phosphate composites, and when the calcium phosphate glasses are crystallized, those rare earth oxides act to accelerate the formation of a large number of crystal nuclei in the interface with the glasses, while inhibiting the growth of crystal grains. As a result, the calcium phosphate glass is crystallized into aggregates of fine crystal grains. In this manner, the strength and the toughness are improved markedly.

DETAILED DESCRIPTION OF THE INVENTION

A detailed description will hereunder be given on dental material obtained by using calcium phosphate glass-ceramics according to this invention.

Basic starting materials of the calcium phosphate system used in this invention are compounds containing calcium, which produces CaO by calcination, and compounds containing phosphorus, which also give oxides of phosphorus, such as $P_2O_5$, by calcination. As calcium-containing compounds, calcium oxide, calcium hydroxide, calcium carbonate, calcium hydrogencarbonate, basic calcium carbonate, etc., and calcium salts of organic acids, such as calcium oxalate, calcium acetate, etc. may be used. As phosphorus-containing compounds, for example, orthophosphoric acid, metaphosphoric acid, and polyphosphoric acids, such as pyrophosphoric acid, triphosphoric acid, trimetaphosphoric acid, tetrametaphosphoric acid, or ammonium salts of these phosphoric acids, etc. may be used. Also, calcium salts of phosphoric acids such as calcium hydrogenphosphate, calcium dihydrogenphosphate, calcium phosphate, calcium pyrophosphate, calcium polyphosphate, various apatites, may be used as a single compound or by mixing with the other calcium-containing compounds of phosphorus-containing compounds.

The ratio to calcium-containing compounds to phosphorus-containing compounds for use is 0.35–1.7, preferably 0.45–0.7, in atomic ratio of calcium to phosphorus Ca/P in those compounds. When the above-mentioned atomic ratio exceeds 1.7, the melting point becomes extremely high, and vitrification does not occur. As a result, devitrification occurs during cooling. When devitrification occurs, coarse crystal grains of calcium phosphate come to be contained in the structure, thus inviting the undesirable outcome of seriously worsening brittleness as well as of degraded toughness. On the other hand, when the atomic ratio is lowered below 0.35, while the melting point gets lowered and vitrification becomes facilitated, it takes a long time for the crystallization process, that will be mentioned later, with the additional undesirable outcome of chemical instability caused by liberation of phosphoric acid.

Next, rare earth oxides which are added in order to improve the strength and toughness of calcium phosphate crystalline glasses are 0.05 to 10 wt. pt. in amount compared with 100 wt. pt. of calcium phosphate composites. They are added in the form of oxides, and also of carbonates, hydroxides, nitrates, etc. The rare earths are used by mixing one type or two or more types of them, and it is desirable that yttrium (Y), lanthanum (La), or cerium (Ce) is contained in the rare earths to be mixed. When the amount added is less than 0.05 wt. pt., the increase in strength and toughness is insufficient. On the other hand, when it exceeds 10 wt. pt., the melting point of the mixture gets higher and the viscosity of the melt increases, making it difficult to cast.

For dental materials, this invention is characterized in that into the above-mentioned starting materials, one component, or two or more components, preferable two to three components, which are selected from the following compounds are added as coloring components. The compounds mentioned above are those which contain iron, manganese, cerium, titanium, nickel, zinc, cobalt, tungsten, chromium, and vanadium as coloring components for the foregoing starting materials, and which can be turned into oxides during the melting process that will be mentioned later. Such compounds are, for example, oxides, acetates, sulfides, nitrates, carbonates, and ammonium salts of the metals listed above.

Desired color tones can be obtained by mixing one component or two or more components of those coloring components, with a specified ratio. When the coloring components are two or more in type, the hue varies depending on the combination and composition ratio of the compounds. Also, in the above-mentioned case, the shade (darkness) of color varies depending on the adding ratio of the total amount of the coloring components.

The total amount of the coloring components added is 0.01 to 15 parts by weight (wt. pt.), preferably 0.3 to 5 wt. pt., compared with 100 wt. pt. of the calcium phosphate starting material, in calculation in terms of oxide. When the amount added is less than 0.01 wt. pt., the coloring is insufficient and the color is blocked out by white color of calcium phosphate glass-ceramics. On the other hand, when it exceeds 15 wt. pt., not only the coloring after crystallization becomes too dark, but also the melting point of the mixture gets higher and the viscosity of the melt increases, making it difficult to cast it.

As was mentioned above, the dental materials using calcium phosphate glass-ceramics provided by this invention are capable of giving the color tone close to that of natural teeth through the addition of the coloring components. Furthermore, through still further addition of $Al_2O_3$ and/or $SiO_2$, the aesthetic appearance can be enhanced more. For such addition, in addition to oxides, hydroxides, hydroxy-carbonates, carbonates, nitrates, ammonium salts, etc. which become oxides during the melting process are used. These components act to facilitate the color at the time of coloring through the reaction of the coloring components with the calcium phosphate components which are the starting materials. The amount of such assisting components is 10 wt. pt. or less, preferably 1 to 5 wt. pt., compared with 100 wt. pt. of a calcium phosphate as starting material, according to the calculation conducted by converting into oxides. When the amount added is more than 10 wt. pt., the result is undesirable because the viscosity of the melt becomes high and casting becomes difficult.

An example of the method for preparing the dental and bone materials by calcium phosphate glass-ceramics according to this invention will be given below.

Calcium compound, phosphate-containing compound, and rare earth compound are weighed out, respectively, and mixed throughly. When necessary, coloring component assistant and coloring agent are also weighed out and mixed together with the foregoing components. If those components are in a solid state, they are pulverized before mixing. The mixture of starting materials thus obtained is placed in an appropriate vessel, and melted by heated to above 900 degrees centigrade, preferably 1000–1600 degrees centigrade. For the vessel for melting, any quality of material may be used so long as it is hardly damaged (eroded) by the melt. Platinum is most desirable, but since it is high in price, alumina or zirconia vessels may be used although such vessels may suffer slight erosion on their internal surfaces. The melting temperature varies depending on the ratio of the starting materials. However, when the above-mentioned range of temperature is used, the viscosity of the melt can be maintained sufficiently low. Thus, it is optimum for casting. When the melting temperature goes up, and particularly when it exceeds 1700 degrees centigrade, the phosphorus component starts to be evaporated, and the composition changes gradually to have an excessive content of calcium, whereby pushing the melting point upward gradually. Accordingly, care should be taken in this regard. The melt mentioned above is cooled into a vitreous state. For cooling, any method may be used.

The vitreous material thus obtained is either cast-formed into dental material by using centrifugal casting process, pressure casting process, vacuum pressure casting process, etc. based on the lost wax process, or processed into a specified form through compression molding after pulverized into fine grains.

When the casting process is employed, the melting temperature used is above 900 degrees centigrade, preferably 1000–1600 degrees centigrade. The lost wax process is the method to be used for metallic materials. However, if calcium phosphates used in this invention are 0.35–1.7 in the range of Ca/P, their melting point and viscosity are almost the same as those of metallic materials. Therefore, they are applicable to casting by the lost wax process.

Because tooth-crowns or bones, etc. thus obtained are glassy in state, they are processed for crystallization. The investment are heated in appropriate heating equipment, such as electric furnace. The heating rate is 50°–400° C./hr, the heating temperature is 500–900 degrees centigrade, and the duration is 0.5–100 hr. Through this crystallization process, the coloring component reacted with the calcium phosphate component is incorporated into crystals and stabilized. At the same time, it gives the color tone close to that of natural teeth. And moreover, by the effect of adding rare earth oxides, many fine crystals of 0.05–0.5 microns in size are produced and cause high strength and toughness.

The dental and bone materials by calcium phosphate glass-ceramics in accordance with the present invention are characteristic in the following points in comparison with conventional dental materials.

1. They are the calcium phosphate materials which are ideal as dental or bone material since their component materials and characteristics are similar to those of natural teeth or bones, and their color tones come out to be approximate to those of natural teeth, thereby contributing to the improvement of aesthetic appearance.

2. When rare earth oxides are contained, the strength and toughness are upgraded.

3. The coloring components react with starting materials. Then, the coloring is effected as a result of this reaction, and at the same time, the coloring components become insoluble. Besides, the coloring components are incorporated into crystals. Accordingly, there is absolutely no possibility of occurence of elution of the coloring components.

4. For the addition of the coloring components into the starting materials, exactly the same process as is used in ordinary case can be used. This makes the use of complicated coloring processes as used for porcelain facing completely unnecessary.

Hereunder, a description will be given of this invention with reference to embodiments.

EMBODIMENT 1

Calcium carbonate and phosphoric acid were weighed out in a manner to obtain 0.55 in atomic ratio of calcium to phosphorus Ca/P, and they were mixed. Into 100 wt. pt. of the mixture obtained as mentioned above (measured by converting into calcium phosphate), yttrium nitrate was weighed out in the amount of 1.3 wt. pt. by measuring it in terms of $Y_2O_3$ (i.e., in $Y_2O_3$ equivalent), and added to the above. Then, the mixture of all of the foregoing components was kneaded thoroughly, and melted in a platinum crucible at 1300 degrees centigrade for one hour. At the same time, the mold in the form of $3 \times 4 \times 30$ mm that was prepared by the lost wax process was preheated to 500 degrees centigrade and set in the centrifugal casting machine. Then, the above-mentioned melt was poured into that mold after the melt was cooled at 1100 degrees centigrade, for casting.

After cooling, the cast glass was taken out of the investment, and crystallized by heating it up to 680 degrees centigrade with a heating rate of 300° C./hr in an electric furnace and by keeping it as it was for 5 hours.

In the microscopy of the fracture of the foregoing crystallized product conducted after measuring the modulus of rupture of this product, fine crystals (0.1 micron in average) were observed.

EMBODIMENT 2

Crystallized glass was obtained by the same method as in EMBODIMENT 1, except that the coloring component 0.6 wt. pt. of mixed powder of 40 wt. % of $CeO_2$, 40 wt. % of $TiO_2$ and 20 wt. % of NiO was added together with 0.3 wt. pt. of $SiO_2$.

EMBODIMENT FOR COMPARISON 1

Crystallized glass was obtained by the same method as in EMBODIMENT 1, except that yttrium nitrate was not added.

Table 1 shows the values of three-point modulus rupture and fracture toughness obtained for the glass-ceramic prepared in EMBODIMENTS 1 and 2, and EMBODIMENT FOR COMPARISON 1. The values of fracture toughness were obtained by using the Vickers indentation method, and they are indicated by the ratio by setting the value for EMBODIMENT FOR COMPARISON 1 as 1.

As is apparently seen in Table 1, through the addition of rare earth oxides, a significant improvement in strength as well as in toughness is effected. The same effect is shown also when the coloring components are added.

TABLE 1

|  | Embodiment 1 | Embodiment 2 | Embodiment for Comparison 1 |
|---|---|---|---|
| Bending strength (kg/cm$^2$) | 2310 | 2180 | 1100 |
| Breaking toughness value ratio | 1.6 | 1.5 | 1.0 |

We claim:

1. Dental materials of calcium phosphate glass-ceramics consisting of:
   calcium phosphate composite wherein the atomic ratio of calcium to phosphorus Ca/P is 0.35–1.7; and
   rare earth oxides wherein the content of said rare earth oxide component is 0.05–10 wt. pt. per 100 wt. pt. of calcium phosphate composite whereby the mechanical strength of the dental materials is improved.

* * * * *